United States Patent [19]

Alexiou et al.

[11] 4,371,694

[45] Feb. 1, 1983

[54] AROMATIC COMPOUNDS AND THEIR MANUFACTURE

[75] Inventors: Michael S. Alexiou, Uxbridge; Philip I. Brittain, Bray; John H. P. Tyman, Uxbridge, all of England

[73] Assignee: Brent Chemicals International Limited, Iver, England

[21] Appl. No.: 197,772

[22] PCT Filed: Nov. 7, 1979

[86] PCT No.: PCT/GB79/00183

§ 371 Date: Jul. 1, 1980

§ 102(e) Date: Jul. 1, 1980

[87] PCT Pub. No.: WO80/00963

PCT Pub. Date: May 15, 1980

[30] Foreign Application Priority Data

Nov. 7, 1978 [GB] United Kingdom ............... 43411/78

[51] Int. Cl.³ .................. C07D 221/14; C07D 311/06; C07C 101/66
[52] U.S. Cl. ................................ 546/100; 260/465 E; 260/508; 562/433; 562/457; 562/458; 549/232
[58] Field of Search ...................... 562/433, 457, 458; 260/345.2, 508, 465 E; 546/100

[56] References Cited

U.S. PATENT DOCUMENTS 2,426,577 8/1947 Sealera et al. ..................... 260/378
4,017,511 4/1977 Williams ......................... 260/326 N
4,163,747 8/1979 Schroeder et al. ................. 260/378

FOREIGN PATENT DOCUMENTS 2607036 9/1976 Fed. Rep. of Germany ...... 260/378
2537798 11/1976 Fed. Rep. of Germany ...... 260/378
1557945 1/1969 France ............................. 260/345.2
2213269 2/1974 France ............................. 260/378
48-37125 11/1973 Japan .............................. 260/345.2
1550985 8/1979 United Kingdom ........... 260/326 N

OTHER PUBLICATIONS

Okazaki et al., "Chemical Abstracts", vol. 51, Abstract No. 8050g.
Wood et al., "J. Chem. Soc.", vol. 3, pp. 3373-3378, (1962).
Fendler et al., "J. Org. Chem.", vol. 33, p. 977, (1968).
Kimura et al. (I), "Chem. Ab.", vol. 62, Ab. No. 27127c, (1965).

Primary Examiner—John Doll
Attorney, Agent, or Firm—Arnold, White & Durkee

[57] ABSTRACT

Compounds of Formula I or Formula II

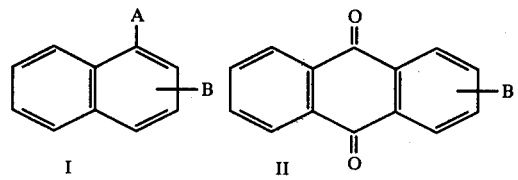

where A is an electron withdrawing group and B is a secondary or tertiary amino group or the group OD where D is H, aryl or an aliphatic group are made by reacting a corresponding compound of Formula Ia or Formula IIa

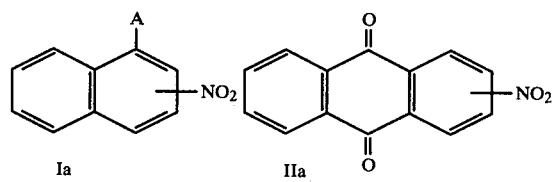

in a solvent with a reagent selected from organic primary and secondary amines and compounds of the formula MOD where M is an alkali metal and A and D are as defined above. In this process the nitro group and the group B in Formula I and Ia are in the 2- or 4- position and the compounds of Formula I, Ia, II and IIa may optionally be further substituted. Preferably a primary or secondary amine is reacted with a compound of formula Ia, preferably using dimethylformamide as solvent. The process can result in the production of novel compounds, including (1) Compounds of Formula III

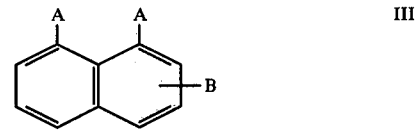

wherein each group A is $CO_2H$ or an alkali metal, amine or ammonium salt thereof or the two groups A together form a carboxylic anhydride group and B is in the 2- or 4-position and is OD, where D is hydrogen or an aliphatic group or is a secondary or tertiary amine group, (2) compounds of Formula IV

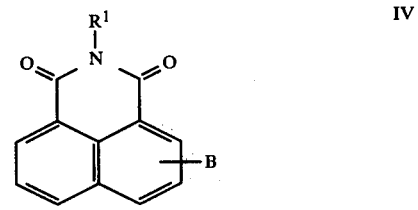

where B is the group OD or the group $NR_2R_3$ and wherein at least one of $R_1$ and D or at least one of $R_1$, $R_2$ and $R_3$ comprise a solubilizing group containing a primary amino, carboxylic, sulphonate or phosphate ester group in the form of an alkali metal, amine or ammonium salt or is polyalkylene oxide group, the compounds optionally being further substituted.

11 Claims, No Drawings

AROMATIC COMPOUNDS AND THEIR MANUFACTURE

This invention relates to the production of polycyclic aromatic compounds, and to novel compounds so produced, and especially to such compounds substituted by secondary or tertiary amine, hydroxyl or ether groups. The polycyclic system is preferably a naphthalene ring. Such compounds have various uses, for instance as dyes, especially fluorescent dyes, as pharmaceuticals (for instance as anti-malarials), and as intermediates for either. The polycyclic ring can be an anthraquinone ring, the compounds then being useful as dyes or dye intermediates.

The synthesis of many aromatic secondary or tertiary amines can be rather difficult to carry out in an economic manner. For instance the production of a compound such as 4-n-butylamino N-n-butylnaphthyl-1,8-imide may involve forming 4-bromo naphthalic anhydride and then reacting this with n-butylamine to form the desired compound, but this suffers from the disadvantages that it is a multistage process, it is difficult to make the bromo compound in good yield, and the use of a bromo derivative necessarily incurs considerable expense.

It is known to make some aromatic amino compounds starting from the corresponding aromatic nitro compound but the methods of conversion again are not entirely satisfactory. Thus while primary amino compounds can often be produced simply by catalytic or chemical reduction, if a secondary or other amino compound is required then the primary amino compound has to be subjected to subsequent reaction, such as with an alkyl halide. In theory a secondary amine can be made in a single stage by reacting the nitro compound with ammonia and an aldehyde and hydrogen and a catalyst under pressure but in practice a mixture of secondary and tertiary amines tends to be produced.

Several processes are known for converting certain nitro-anthraquinones to primary amino anthraquinones. Thus certain nitro anthraquinones can be converted to amino anthraquinones by reaction with sodium sulphite but again the synthesis is not very reliable and only forms a primary amino group.

In British Patent Specification No. 1,524,729 several processes of reducing nitro group in nitroanthraquinones to primary amino group are discussed, and in particular a process is described in which a dinitro anthraquinone is converted to a mono-nitro mono-amino anthraquinone by reaction at a temperature of above 60° C. with ammonia in a dipolar aprotic solvent. It is explained in the specification that the reaction temperature is preferably 100° to 130° C. and that the reaction is preferably conducted by bubbling gaseous ammonia into the solution of dinitro anthraquinone until a total amount of ammonia of up to 50% excess based on the stoichiometric amount has been introduced. For instance in Example 1 complete reaction is said to be achieved after 6 or 7 hours at 120° C. In all the examples a mixture of reaction products is obtained in which the main component is the mono-amino mono-nitro compound. This suggests that one of the nitro groups is activated, for the purposes of the reaction, by the other nitro group.

Whatever the mechanism however the process is restricted to starting with dinitro anthraquinone, it introduces only a primary amine group, and always yields a mixture of products that have to be separated by what is, in practice, a difficult separation technique. Accordingly the process is of no assistance to us in our objective of devising a simple synthesis for the successful economic and easy production of polycyclic aromatic secondary or tertiary amines. It is also our objective to produce other polycyclic aromatic compounds, such as those containing hydroxy or alkoxy substituents.

We have now discovered a new process that appears to be conducted by a reaction mechanism different from any mechanism previously described in the literature for polycyclic aromatic compounds and which is applicable for the production of secondary and tertiary amines, alcohols and alkoxides of naphthalene compounds and also of anthraquinone compounds.

The compounds produced by the process of the invention are compounds of Formulae I or II

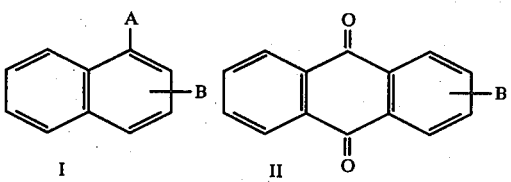

where A is an electron withdrawing group and B is a secondary or tertiary amino group or the group OD where D is H, aryl or aliphatic. B is in the 2- or 4-position in the compounds of Formula I and is generally in the 1-position in the compounds of Formula II, although it may be elsewhere, for instance the 2, 4, 5 or 8 positions. The compounds may contain additional substituents. Thus the compound of Formula I may contain, for instance, substituents A at both the 1- and 8- positions and the compounds of Formula II may contain a substituent B in each end ring and any of the rings may contain optional further substituents as described in more detail below.

In the invention these compounds are produced by a process comprising reacting a corresponding compound of the Formula Ia or IIa

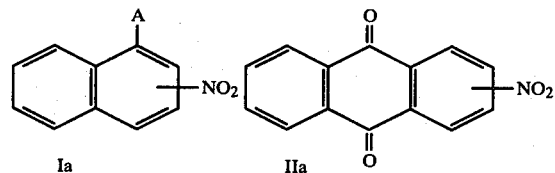

in a solvent with a reagent selected from organic amines and compounds of the formula MOD where M is an alkali metal and A and D are as defined above and the nitro group is in the position to be occupied by the group B in the end product.

The reaction can conveniently be looked upon as a nucleophilic substitution since it seems to be controlled by the same parameters as control nucleophilic substitutions. However we are not limited to the reaction necessarily being a true nucleophilic substitution reaction and the reaction may involve, for instance, the formation of an intermediate carbanion.

The reaction is carried out in the liquid phase preferably in the presence of an inert aprotic solvent with the reactants in solution. The aprotic solvent may be used alone or part of the liquid phase may be provided using excess of the reagent (e.g. using more than 5 moles reagent per mole nitro compound) or a mixture may be used of aprotic solvent and other solvent that is inert to the reactants. Generally at least half the solvent is aprotic and preferably substantially all is aprotic. Mixtures of aprotic solvents may be used. The aprotic solvent or solvent mixture must be inert to the reactants and the desired compound. Solvents can be selected from tetrahydrofuran, glycol ethers, dimethylsulphoxide (DMS0), N-methylpyrrolidone, sulpholane, hexamethylphosphoric triamide, nitrobenzene and orthodichlorobenzene. The preferred solvent for reaction with amines is dimethylformamide (DMF), for purity, yield and convenience reasons. DMF and other amide solvents, and solvents such as DMSO, are not inert to some compounds MOD and when the reactant is MOD the solvent is preferably an ether, for instance a glycol ether preferably the dimethyl ether of ethylene glycol (Diglyme).

The reaction medium should be substantially anhydrous and the reaction should be carried out in the substantial absence of air, oxygen or other oxidising gas. Preferably the reaction is carried out under nitrogen or other inert gas. For instance the reaction vessel and mixture may be purged with nitrogen and the reaction then carried out under an atmosphere of inert gas. Preferably the reaction is carried out at or slightly above atmospheric pressure, e.g. 1 to 2 atmospheres.

The amount of amine or other reagent should be at least the stoichiometric amount required for reaction with the nitro and, if appropriate, with any other substituents in the ring. Generally the amount is more than the stoichiometric amount. Preferably the amount of amine or other reagent is at least twice the stoichiometric amount required, e.g. 2 to 15 times.

The reaction temperature may influence the end products obtained. Generally it is between 0° and 140° C., although temperatures of ambient (e.g. 20° C.) or more are preferred. When the reagent is MOD suitable temperatures are 50° to 100° C. When the reagent is an amine suitable temperatures are 20° to 120° C. When the reaction permits, it is desirable for the reaction temperature to be below 55° C.

The reaction mixture is preferably stirred throughout the reaction period. Although the reaction may occur substantially immediately upon mixing the amine or other reagent with the nitro compound, so that reaction periods of 1 to 10 minutes may be adequate, preferably longer periods are used, e.g. 1 to 10 hours, preferably 2 to 5 hours. Routine experiment will determine the optimum reaction period for any particular reaction temperature since if the reaction is conducted for too long at any particular temperature there is increased risk of unwanted by-products being formed.

When the reagent has the formula MOD, D is preferably aliphatic so the product is an ether. D may be lower alkyl, allyl or alkenyl. It may be substituted, for instance by a second group OM, so that the reagent has the formula MODOM, a diether then being formed. The alkali metal M is preferably sodium but could be, for instance, potassium. The reagent MOD (or MODOM) is preferably formed previously and introduced into the reaction medium in substantially anhydrous form.

Preferably the reagent is a primary or secondary amine. When the reagent is a primary amine it will generate a secondary amino group B while if it is a secondary amine it will generate a tertiary amino group B. The primary or secondary amine reagent can itself be hydrazine or a substituted hydrazine, thereby generating a hydrazine group.

Broadly, amino reagents used in the invention may have the formula $R^2R^3NH$ (with the result that B is $R^2R^3N-$) wherein $R^2$ may represent $-NR^4R^5$, aryl or aliphatic group, $R^3$, $R^4$ and $R^5$ may each individually represent H, aryl or aliphatic groups or $R^2$, $R^3$ and the nitrogen atom to which they are attached may form a heterocyclic ring. When $R^2$ represents hydrazine then $R^4$ at least is preferably hydrogen since this gives the opportunity of two molecules of the compound of formula II reacting with one molecule of the hydrazine. Thus in the end products B may have the formula $-N(R^3)NR^5R^6$ wherein $R^3$ and $R^5$ are hydrogen or aliphatic and $R^6$ is a polycyclic aromatic ring structure such as in Formula I or II, the resultant compound for instance being a symmetrical hydrazine disubstituted by naphthyl 1,8-imide.

Aliphatic radicals $R^2$ to $R^5$ or D may be aralkyl, alkyl, cycloalkyl, alkenyl or allyl. They may be short chain, lower, radicals e.g. containing up to 4 carbon atoms but broadly they may contain up to, for instance, 18 carbon atoms. Any may be substituted by, for instance, carboxylic, sulphonic, phosphate ester, hydroxy or hydroxyalkoxy groups. For instance any of these substituents may carry a recurring alkoxide chain, for instance being obtained by the condensation of ethylene oxide and/or propylene oxide onto a hydroxy alkyl group. Long chain (e.g. $C_{6-18}$) aliphatic groups are preferably highly branched. They may be benzyl.

Any of the benzene rings in the compounds used as starting materials and made as end products may contain optional substituents although if there is a substituent ortho to a nitro group then this substituent should be sufficiently small that it does not create steric interference during the reaction. Optional substituents that may be present in any ring may be as described above for $R^2$ to $R^5$ and may be selected from, for instance, alkyl, alkoxy, hydroxyalkoxy, cycloalkyl, alkenyl, alkaryl, aryl, hydroxy and halogen. Substituents such as alkyl may themselves be substituted, for instance, trifluoromethyl. Aryl may be substituted by, for instance, any of the substituents listed but also by solubilising groups such as a sulphonic acid group.

The invention can be applied to the production of anthraquinones, namely the compounds of Formula II. The starting materials, of Formula IIa, generally contain a single nitro group generally in the 1-position but may contain more than one nitro group. The compounds of Formula II generally contain only one amino group (this being secondary or tertiary) or hydroxy or ether group. The compounds are useful as, for instance, dyes.

A particularly surprising and important feature of the invention is the discovery that if a naphthalene ring carries an electron withdrawing group A in the 1-position, and preferably also a second group A preferably in the 8-position, then a 2 or 4 nitro group can be replaced by a group B as defined above under the defined reaction conditions. The resultant compounds of formula I are useful as dyes, many of them being fluorescent and many having very useful solubility properties. They may be used in compositions and for purposes such as those described in U.S. Pat. Nos. 2,953,530 and 3,915,885. Compounds that are not dyes can be used as intermediates for the production of dyes.

The or each electron withdrawing group A can be a cyano group or a sulphonic acid group but preferably comprises a carbonyl group, with the carbonyl group preferably substituted direct onto a ring. The or each carbonyl group may be provided by a carboxylic acid group or, preferably, a carboxylic acid salt (generally of sodium or other alkali metal or a non-interfering amine), an anhydride or an imide group. When as is preferred the compound of Formula I is substituted by two groups A in the 1- and 8-positions these may be present as carboxylic acid or salt groups or they may be present as a cyclic imide or anhydride with the 1 and 8 carbon atoms of the naphthalene ring. The radicals providing the group or groups A may remain unchanged during the reaction or may be reacted to form other radicals. Thus if the starting material of Formula Ia is a 1,8-cyclic imide the end product usually is the same 1,8-cyclic imide, both generally being N-substituted. If the starting material is an anhydride or dicarboxylic acid salt the end product of Formula I may be a 1,8-cyclic imide, generally N-substituted, or a 1,8-dicarboxylic acid or salt thereof or a 1,8-dicarboxylic anhydride.

Typical reactions according to the invention are illustrated below in which for simplicity the naphthalene ring is assumed always to be substituted in the 4-position by nitro and to be unsubstituted elsewhere, but of course corresponding reactions also exist for the corresponding 2-nitro compounds and the compounds in which there are other substituents in the naphthalene ring that do not interfere with the reaction. In the following reaction schemes $R^2$, $R^3$ and D may be as described above and $R^1$ may be an aliphatic group as described above or amino.

REACTION SCHEME 1

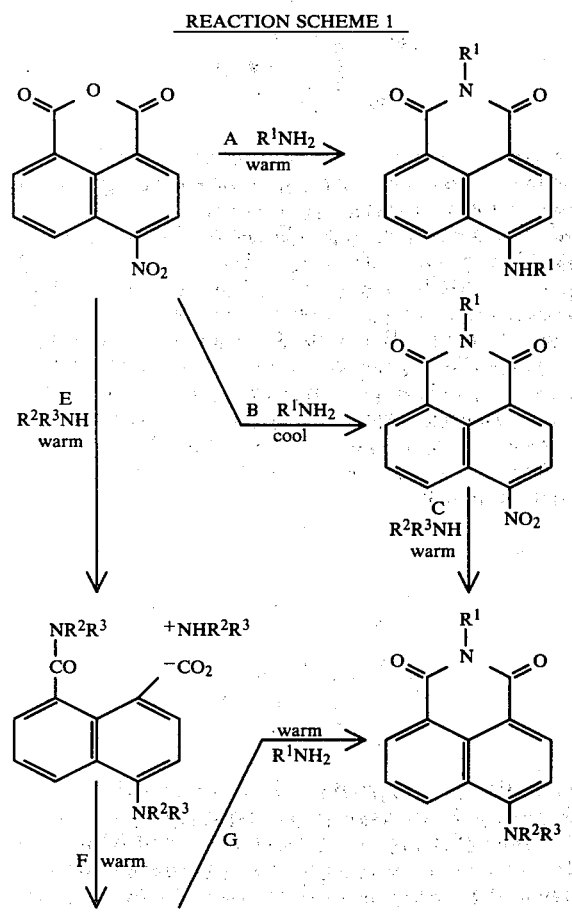

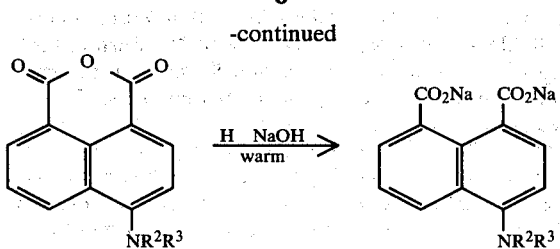

REACTION SCHEME 2

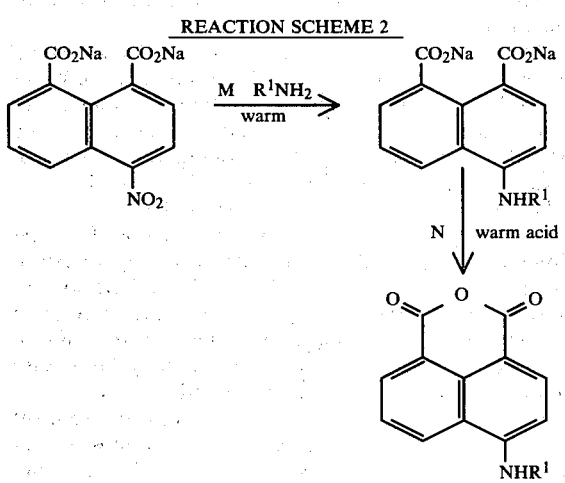

REACTION SCHEME 3

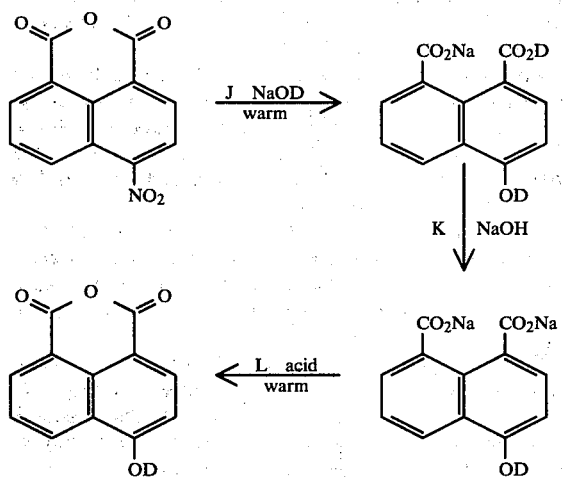

Referring to reaction scheme 1, reaction of the anhydride with a primary amine results in the formation of an imide, the 4-nitro group remaining unconverted at lower temperatures or being converted to a secondary amine group at higher temperatures. Preferably $R^1$ is a straight chain alkyl group. Reaction A occurs best at temperatures of 40° to 140° C. and reaction B at temperatures 0° to 35° C. For instance reaction A may be conducted at about 50° C. in DMSO or 120° C. in DMF while reaction B may be conducted at about 0° C. in DMSO or 20° C. in DMF. Reaction C advantageously can be conducted using solvents and temperatures similar to reaction A.

If the anhydride is reacted with a secondary amine then the anhydride ring is opened as shown in reaction E to form an amide and salt. If the reaction temperature is low, e.g. 0° to 35° C., the 4-nitro group may remain unconverted but at higher temperatures, e.g. 40° to 140° C. the 4-nitro group is displaced by an amino group, as shown in reaction E. Preferably reaction E is conducted in DMF at temperatures of 80° to 140° C. Further heating of the salt formed in reaction E results in reformation of the anhydride ring, as shown in reaction F. This heating may be conducted at 40° to 140° C., preferably 100° to 140° C. The anhydride can be split open to form the disodium or other alkali metal salt by treatment with warm alkali, e.g. at 40° to 140° C. preferably about 80° C. The resultant disodium salt can be converted to the anhydride by heating with warm mineral acid (e.g. as shown in reaction N in reaction scheme 2).

The conditions for reaction M in reaction scheme 2 are preferably similar to those for reaction A and result in the formation of a disodium salt of the 4-amino substituted compound and this salt can then be cyclised to the anhydride by reaction N by warming with a mineral acid, for instance sulphuric or hydrochloric acid, generally at 40° to 140° C. preferably about 100° C.

Referring to reaction scheme 3, reaction J is best conducted using sodium alkoxide at a temperature of 40° to 140° C., preferably 50° to 100° C. The solvent must be inert to the reaction conditions and so an ether is preferred, preferably diglyme (dimethylether of ethylene glycol). The product will generally be a ester sodium salt as shown in reaction J and this can be converted to the disodium salt by conventional treatment with sodium hydroxide, as shown in reaction K, e.g. at 40° to 140° C., preferably about 100° C. By adjusting reaction conditions it may be possible to obtain the disodium salt direct. The disodium salt can then be converted to the anhydride as in reaction N, and then converted to the imide as in B.

Reaction J can also be conducted starting from the corresponding 4-nitro cyclic imide, instead of anhydride, and whilst this reaction can be conducted to leave the imide unchanged and replace the nitro group by OD there is a tendency for the imide group to be split and so the yields may be less satisfactory.

All the processes are capable of being operated to give the desired end products in good yield and purity. Isolation can be conducted easily, for instance by distilling off the solvent and recrystallising from a suitable liquor, often isopropanol.

Preferred processes according to the invention are processes A and C above and comprise reacting a 4-nitro naphthyl compound substituted in the 1 and 8 positions by carbonyl groups (preferably 4-nitro naphthyl-1,8-anhydride or imide) in the liquid phase in solution and in an aprotic solvent, preferably dimethyl formamide, in the substantial absence of air and water at a temperature of 40° to 120° C. with at least 2 moles of an amine of the formula $R^2R^3NH$ for a period of 10 minutes to 6 hours. This very simple synthesis can easily be operated so as to give a substantially pure product that is eminently suitable for use in systems such as those described in U.S. Pat. Nos. 2,953,530 and 3,915,885 and avoids the problems inherent in all the known processes for the manufacture of such compounds.

The nitro substituted aromatic compounds are often known compounds and those that are not known can be made by processes analogous to those processes that are known for known compounds. For instance, the starting compound for reaction A may be made by nitration of acenaphthene followed by oxidation of this, for example by the general method described by Mitsuo Okazaki, Tatsuo Tanaka and Setsuro Taniguchi (Tokyo Inst. Technol)-Yuki Gosei Kagahu Gosei Shi 14, 344–6 (1956). Compounds such as the starting material of reaction C may also be made by oxidising 5-nitro acenaphthene to 4-nitro naphthalic anhydride and converting this to an imide by reacting with the primary amine or with ammonia at low temperature for an appropriate period.

The invention may be applied to the production of both new and old compounds and an advantage of the invention is that it permits the convenient production of compounds having much more varied substituents than has generally been possible with known methods. For instance 1,8-cycloimides of Formula I wherein the imide nitrogen and/or B carry a long chain aliphatic hydrocarbon group may be made, the group preferably being alkyl and may be branched and/or long chain (e.g. above 10 carbon atoms). Such compounds can have greater oil solubility than the known compounds of this formula that are generally available and this can be very desirable for facilitating the formation of oil based compositions intended for the same general purposes as described in the aforementioned U.S. Patent Specifications. Accordingly the invention includes these novel compounds having increased oil solubility and also compositions containing them dissolved in simple oils, such as kerosene, and methods of using them.

Other novel compounds according to the invention are compounds of formula I containing at least one water solubilising group.

One class of novel compounds of the invention are compounds of formula III

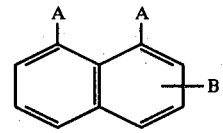

III wherein each group A is $CO_2H$ or an alkali metal, amine or ammonium salt thereof or the two groups A together form a carboxylic anhydride group and B is the 2- or 4-position and is OD, where D is H, aryl or an aliphatic group or is a secondary or tertiary amine group $-NR^2R^3$ where $R^2$ and $R^3$ are as described above, the compound optionally being further substituted. Generally B is in the 4-position and is a dialkylamino or alkoxy group and there are no further substituents. Generally these compounds are fluorescent and many, especially those involving water soluble salts of carboxylic acid groups A, are water soluble.

Other preferred novel compounds are compounds of the Formula IV

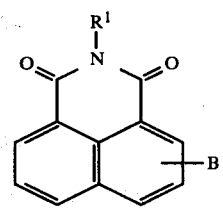

IV where B is the group OD or the group $-NR^2R^3$ and D, $R^1$, $R^2$ and $R^3$ are as described above and wherein (a) at least one of $R^1$ and D or (b) at least one of $R^1$, $R^2$ and $R^3$ comprise a solubilising group containing a primary amino ($NH_2$) group or a carboxylic, sulphonate or phosphate ester group in the form of an alkali metal, amine or ammonium salt or is a polyalkylene oxide group. Many of these also are fluorescent and many also are water soluble. Preferably at least one of the groups $R^1$ and D or $R^1$, $R^2$ and $R^3$ is a polyoxyalkylene chain, generally of the formula $—(CH_2CH_2O)_nH$ where n is greater than 1, e.g. 2 to 10, or is a group $—R^6X$ where $R^6$ is alkylene, generally of 1 to 4 carbon atoms preferably 1 or 2 carbon atoms and X is a carboxylic, phosphate ester or sulphonate group in the form of an alkali metal, amine or ammonium salt. Preferably $R^1$ is a solubilising group and there is a second solubilising group in the molecule, generally consisting of D, $R^2$ or $R^3$.

Those groups containing alkylene oxide chains may be made by alkoxylation of compounds in which $R^1$, $R^2$, $R^3$ or D is, for instance, a hydroxyalkyl group or where D is a hydroxy group. Those compounds where $R^1$, $R^2$ or $R^3$ contain a carboxylic, phosphate ester or sulphonate group can conveniently be made by one of the reactions illustrated above using an appropriately substituted amine, for example taurine or glycine in the form of their sodium salts.

The following are some examples of the invention.

EXAMPLE 1

4-Nitronaphthalic anhydride is prepared from acenaphthene by the method described by Okazaki et al (see above) involving nitration of acenaphthene, oxidation to 4-nitronaphthalic acid and heating of the acid at 120° C. for 4 hours to give 4-nitronaphthalic anhydride.

4-Nitronaphthalic anhydride is dissolved in the minimum of dimethyl sulphoxide (D.M.S.O.). Methylamine is added in the ratio of 9 moles of amine per mole of anhydride. Addition of amine and subsequent stirring is carried out at 50° C. in the absence of air by passing nitrogen slowly through the reaction vessel so that the pressure of nitrogen in the apparatus is greater than atmospheric pressure. The reaction mixture is stirred at ambient temperature for 3–4 hours, although the reaction appears to be virtually instantaneous. D.M.S.O. is removed under a reduced pressure by distillation (60° C. and 1 mmHg pressure) with passage of nitrogen through the distillation apparatus to act as a "leak". The solid remaining when distillation was complete was a mixture of two or more components which were separated by column chromatography using silica gel (70–230 mesh) as the absorbent and an 80/20% mixture of chloroform and ethyl acetate as the eluent. The major component separated is 4-methylamino-N-methylnaphthyl-1,8-imide. This was found to have a melting point of 261° to 262° C. (literature 258° to 260° C.) and an analysis C69.0%, H5.08% and N11.3% (theoretical C70.0%, H5.0%, N11.6%). The infrared, proton nuclear magnetic resonance and UV spectra were obtained and confirmed the structure. The product was obtained in 71% yield, based on 4-nitronaphthalic anhydride.

As will be apparent, this is an example of reaction A from reaction scheme 1.

Instead of isolating in the described manner, isolation can also be conducted by distilling off the solvent and crystallising the residue from isopropanol.

A similar process can be conducted under broadly similar conditions to give end products as shown in reaction scheme 1, such end products being substituted in the 4-position by an amino group $—NR^2R^3$ and, when appropriate, on the imide nitrogen by $R^1$. In every instance the proton nuclear magnetic resonance, infrared and ultraviolet spectra were as expected and the elemental analysis was substantially accurate. The conditions and results are summarized in Table 1.

TABLE 1

| Experiment No. | Reaction Route | Solvent | Temp (°C.) | Duration (hours) | Moles amine |
|---|---|---|---|---|---|
| 1 | A | DMF | 120 | 5 | 9 |
| 2 | A | DMF | 120 | 5 | 9 |
| 3 | A | DMSO | 50 | 4 | 9 |
| 4 | A | DMSO | 50 | 4 | 9 |
| 5a | B | DMSO | 0 | 3 | 5 |
| 5b | C | DMSO | 20 | 3 | 5 |
| 6a | B | DMSO | 0 | 3 | 5 |
| 6b | C | DMSO | 20 | 3 | 5 |
| 7a | E | DMF | 120 | 3 | 5 |
| 7b | F | DMF | 120 | 3 | 5 |
| 8 | A | DMF | 100 | 3 | 5 |
| 9 | A | DMF | 80 | 5 | 5 |
| 10 | A | DMF | 80 | 5 | 5 |

| Experiment No. | $R^1$ | $R^2$ | $R^3$ | m.p. (°C.) end product |
|---|---|---|---|---|
| 1 | $CH_3$ | H | $CH_3$ | 261–262 |
| 2 | $nC_4H_9$ | H | $nC_4H_9$ | 127–128 |
| 3 | $nC_6H_{13}$ | H | $nC_6H_{13}$ | 90–91 |
| 4 | $nC_{10}H_{21}$ | H | $nC_{10}H_{21}$ | 93–95 |
| 5a | $nC_4H_9$ | — | — | — |
| 5b | $nC_4H_9$ | H | $nC_{10}H_{21}$ | 109–110 |
| 6a | $nC_4H_9$ | — | — | — |
| 6b | $nC_4H_9$ | $C_2H_5$ | $C_2H_5$ | orange oil |
| 7a | — | $C_2H_5$ | $C_2H_5$ | 118–120 |
| 7b | — | $C_2H_5$ | $C_2H_5$ | 190–192 |
| 8 | $CH_2CH_2SO_2Na$ | H | $CH_2CH_2SO_2Na$ | >360; |
| 9 | $NH_2$ | H | $NH_2$ | >360; |
| 10 | $CH_2CO_2Na$ | H | $CH_2CO_2Na$ | >360; |

The products of Experiments 8, 9 and 10 were water soluble. The product of Experiment 8 gave a yellow solution having absorption maxima at 210 and 430 nm. The product of Experiment 9 gave a green solution having absorption maxima at 284 and 400 nm. The product of Experiment 10 gave a green solution having absorption maximat at 323 nm.

EXAMPLE 2

A process similar to Experiment 2 of Example 1 was conducted using the solvent, temperature, reaction route, and duration as in Experiment 2 but using 9 moles amine per mole nitro starting compound and using 2-nitronaphthalic anhydride as the starting material. The resultant 2-butylamino-N-butylnaphthyl-1,8-imide gave a green/yellow solution having absorption maxima at 287, 323, 394 and 440 nm.

EXAMPLE 3

Reaction scheme 3 was conducted by reacting 4-nitrophthalic anhydride with 5 moles sodium ethoxide for 5 hours at 80° C. in diglyme as solvent. The resultant product was a yellow/brown solid having an analysis consistent with the 4-ethoxy substituted ethyl ester sodium salt and could be converted to the disodium salt by reaction with caustic soda and to 4-ethoxynaphthalic anhydride by treatment with warm hydrochloric acid.

EXAMPLE 4

1-Nitroanthraquinone was reacted in DMF at 20° C. with 5 moles n-butylamine for 5 hours. The reaction produced 1-butylamino anthraquinone which was a deep red solid having a melting point of 78° to 79° C.

EXAMPLE 5

To demonstrate the desirability of eliminating air from the mixture, 4-nitronaphthalic anhydride was reacted with n-butylamine in DMSO at 150° C. without exclusion of air. Although the expected di-n-butyl imide was produced a large number of by-products were simultaneously produced which could not be easily removed.

We claim:

1. A process for producing a compound of Formula I

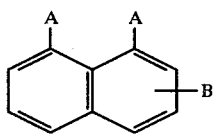

from a compound of formula Ia

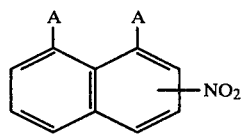

wherein, in each of Formula I and Formula Ia, each substituent A contains a carbonyl group substituted direct into the ring and the two substituents A may be linked to form a cyclic group with the carbon atoms to which they are attached and the groups B and $NO_2$ are each in the same position and are in a position selected from the 2 and 4 positions and, in Formula I, B is selected from secondary and tertiary amino groups, the process comprising reacting the compound of Formula Ia in a substantially anhydrous reaction medium containing a solvent with at least a stoichiometric amount of a reagent selected from organic primary and secondary amines.

2. A process according to claim 1 in which the solvent is an aprotic solvent.

3. A process according to claim 1 in which the reaction is conducted in the substantial absence of oxygen.

4. A process according to claim 1 in which the reaction is conducted at a temperature between 0° C. and 140° C. in the substantial absence of oxygen and in the presence of an aprotic solvent.

5. A process according to claim 4 in which the reaction is conducted at a temperature of from 20° to 120° C.

6. A process according to claim 1 or claim 4 in which the groups A in the compound of Formula Ia together with the carbon atoms to which they are attached form an imide or an anhydride ring.

7. A process according to claim 1 for making a 4-N-substituted amino N-substituted naphthyl-1,8-imide comprising reacting a 4-nitronaphthyl-1,8-imide or anhydride in solution in dimethylformamide in the substantial absence of oxygen or water at a temperature of 40° to 120° C. with a primary amine for a period of 10 minutes to 6 hours.

8. A process according to claim 1 or claim 4 in which the amount of reagent is from 2 to 15 times the stoichiometric amount.

9. A process according to claim 1 or claim 4 in which the reagent is a primary or secondary aliphatic amine and the groups A in the compound of Formula Ia, together with the carbon atoms to which they are attached, form an anhydride or imide ring.

10. A process according to claim 1 or claim 4 in which the reagent is primary aliphatic amine, in the compound of Formula Ia the groups A together with the carbon atoms to which they are attached form an anhydride ring and, in the compound of Formula I, the groups A together with the carbon atom to which they are attached, form an N-substituted imide ring and B is a substituted amino group.

11. A process according to claim 1 or claim 4 in which the solvent is dimethyl formamide.

* * * * *